US00PP22842P2

(12) United States Plant Patent
Heims

(10) Patent No.: US PP22,842 P2
(45) Date of Patent: Jul. 3, 2012

(54) ***SEDUM* PLANT NAMED 'POOL PARTY'**

(50) Latin Name: ***Sedum* sp.**
Varietal Denomination: Pool Party

(75) Inventor: Dan Heims, Portland, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 12/930,958

(22) Filed: Jan. 20, 2011

(51) Int. Cl.
*A01H 5/00* (2006.01)

(52) U.S. Cl. ..... Plt./479

(58) Field of Classification Search ..... Plt./479
See application file for complete search history.

*Primary Examiner* — Kent L Bell
(74) *Attorney, Agent, or Firm* — Jondle & Associates, P.C.

(57) ABSTRACT

A new and distinct hybrid of *Sedum* plant substantially as shown and described, with purple pink flowers in large cauliflower-like inflorescences, blue green leaves with a slight dark edge, strongly upright stems, and a dense, low, mounding habit.

1 Drawing Sheet

Botanical denomination: *Sedum* sp.

Variety designation: 'Pool Party'.

The present invention relates to a new and distinct cultivar of *Sedum* and given the cultivar name of 'Pool Party'. *Sedum* is in the family Crassulaceae. *Sedum* 'Pool Party' originated at the nursery as a seedling that resulted from open pollination of unknown proprietary parents.

Compared to *Sedum* 'Autumn Joy', an unpatented plant, the new variety is much shorter with wider, stiffer stems, shorter internodes, and larger bluer green leaves. The flowers of the new variety are more purple in color.

This new and unique *Sedum* is distinguished by:

1. purple pink flowers in large cauliflower-like inflorescences,
2. blue green leaves with a slight dark edge,
3. strongly upright stems, and
4. a dense, low, mounding habit.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows the new foliage of a 2 year old *Sedum* 'Pool Party' growing in a 2 gallon pot in late May in Canby, Oreg.

FIG. 2 shows the flowers on a 5 year old *Sedum* 'Pool Party' growing on a gravel mound in mid September in Canby, Oreg.

DETAILED PLANT DESCRIPTION

The following is a detailed description of the new *Sedum* hybrid based on observations of two year old specimens grown in a garden in full sun under typical outdoor conditions in Canby, Oreg. Canby is Zone 8 on the USDA Hardiness map. Temperatures range from a high of 95 degrees F. in August to 32 degrees F. in January. Normal rainfall in Canby is 42.8 inches per year. The color descriptions are all based on The Royal Horticultural Society Colour Chart, 5$^{th}$ edition.

Plant:

*Type*.—Herbaceous perennial.
*Hardiness*.—USDA Zone 4 to 9.
*Size*.—43 cm tall from the ground to the base of the inflorescence and 43 cm wide.
*Habit*.—Erect, clumping mound.
*Vigor*.—Excellent.

Stem:

*Number*.—About 11.
*Size*.—32 cm long and 13 mm wide.
*Internode length*.—1 to 3 cm long.
*Color*.—Yellow Green 147C tinted Greyed Purple 187A.
*Texture*.—Succulent.
*Surface*.—Glaucous.

Leaf:

*Type*.—Simple.
*Arrangement*.—Variable.
*Shape*.—Elliptic to obovate.
*Apex*.—Acute.
*Base*.—Cuneate.
*Venation*.—Pinnate.
*Margins*.—Irregularly serrate.
*Blade size*.—Grows to 8 cm long and 5 cm wide.
*Surface*.—Glaucous on both sides.
*Texture*.—Thick, spongy, succulent.
*Petiole*.—Leaves sessile.
*Leaf color*.—Topside between Green N137A and 139A with the vein Yellow Green 147C to Greyed Red 182C near stem; bottom side closest to N138B with vein Yellow Green 147C.

Inflorescence:

*Type*.—Terminal, corymbose, umbel-like.
*Number of flowers*.—Over a 1000 per stem (increases with age).
*Pedicels*.—1 to 3 mm long, 1 mm wide, glaucous, Green N138D.

*Peduncle.*—8 cm tall and grows to 7 mm wide, Yellow Green 147C tinted Greyed Purple 187A, glaucous.

*Size.*—Grows to 15 cm deep and 18 cm wide.

*Bloom period.*—August through September in Canby, Oreg.

Flower bud:

*Size.*—3 mm wide, 5 mm deep.

*Description.*—Ovoid with carpels exposed.

*Color.*—White N155B on petals and Greyed Orange 176A on carpels.

Flower:

*Type.*—Actinomorphic.

*Shape.*—Stellate.

*Size.*—5 mm deep and 5 mm wide.

*Color.*—Red Purple 61A, from the carpel color.

*Corolla description.*—2 mm deep and 5 mm wide, 5 petals, each lanceolate, 3.5 mm long and 1.5 mm wide, margins entire, tip acute, glabrous on both sides, top and bottom side Red Purple 69B.

*Calyx description.*—1.5 mm deep and 2.5 mm wide, campanulate, 5 lobes, divided to the base, margins entire, tip acute, glabrous, Green N138B on both sides.

*Stamen description.*—No stamen.

*Pistil description.*—5 separate prominent carpels, each 6 mm deep and 1.5 mm wide, Red Purple 61A, style 2 mm long, Greyed Purple 187A, stigma rounded, Greyed Purple 187A.

*Fragrance.*—None.

*Lastingness.*—Each stem lasts up to a month.

Fruit:

*Type.*—Ventrally dehiscent follicle, erect, attenuate.

*Fertility.*—None.

*Color.*—Greyed Brown 199A speckled Greyed Purple 187A.

Seed: No seed produced.

Disease and pest resistance or tolerance: Pest and disease resistance are typical for this type of *Sedum.*

I claim:

1. A new and distinct hybrid of *Sedum* plant as herein illustrated and described.

* * * * *

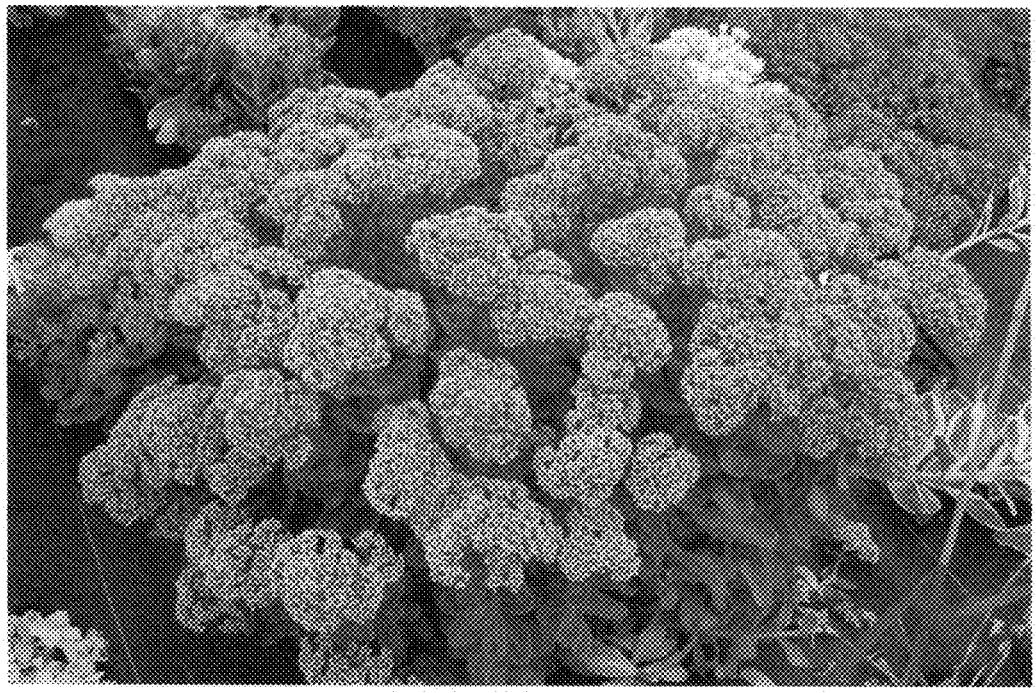

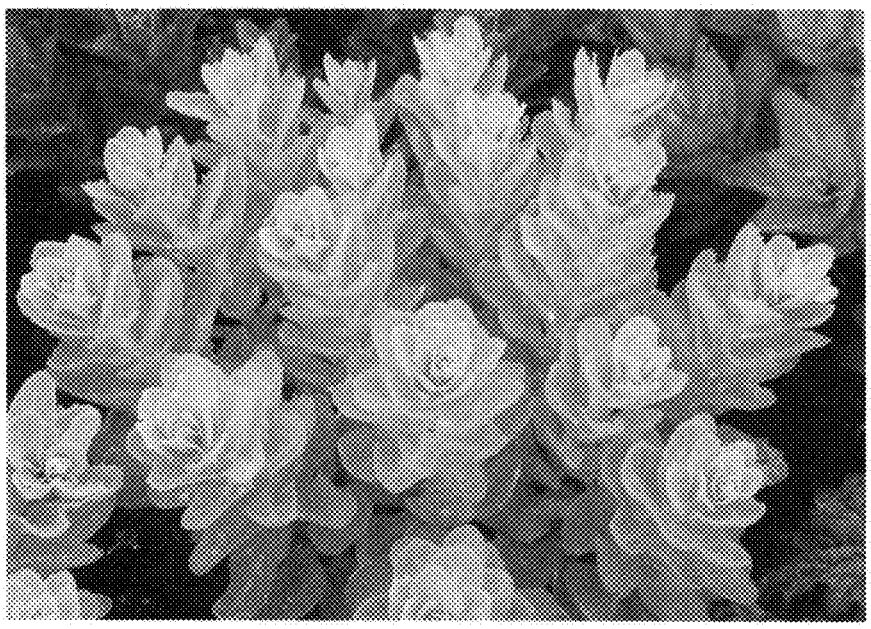
Figure 1 on tip, Figure 2 on the bottom.